US006458766B1

(12) United States Patent
Fenical et al.

(10) Patent No.: US 6,458,766 B1
(45) Date of Patent: Oct. 1, 2002

(54) HALOVIR, AN ANTIVIRAL MARINE NATURAL PRODUCT, AND DERIVATIVES THEREOF

(75) Inventors: William Fenical, Del Mar; Paul R. Jensen, San Diego; David C. Rowley, La Jolla, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/211,877

(22) Filed: Dec. 15, 1998

(51) Int. Cl.$^7$ ............................. A61K 38/08; C07K 7/06
(52) U.S. Cl. ............................. 514/17; 514/2; 530/329; 424/93.1; 424/93.6
(58) Field of Search ....................... 514/17, 2; 530/329; 424/93.1, 93.6

(56) References Cited

U.S. PATENT DOCUMENTS 5,633,230 A    5/1997   Twist et al. ................... 514/15

FOREIGN PATENT DOCUMENTS

EP    0 292 255        5/1988
WO    WO 92/14751      9/1992

OTHER PUBLICATIONS

Bowie et al., *Science*, vol. 247, pp. 1306–1310, 1990.*
Houghten et al., *Vaccines 86*, Cold Spring Harbor Laboratory, pp. 21–25, 1986.*
Atherton and Shepard, *Solid Phase Peptide Synthesis—A Practical Approach*, IRL Press Oxford England, (1989).
Bodanzsky, *Principles of Peptide Synthesis*. 2$^{nd}$ revised edition, Springer–Verlag, New York (1984 and 1993).
Grahm, "Fatty Acid Methyl Ester Profiles for Characterization of Glomalean Fungi and Their Endomycorrhizae," *Applied and Environ. Micriobiol.* 16(1):58–64 (1995).
Green and Wuts, *Protective Groups in Organic Synthesis*, Second edition, John Wiley and Sons, New York, Chapters 2 and 3, (1991).
Reese and Haslam, *Protective Groups in Organic Chemistry*, Plenum Press, New York, Chapters 3 and 4, (1973).
Stewart and Young, *Solid Phase Peptide Synthesis*, 2$^{nd}$ edition, Pierce, Chemical Co., Rockford IL, (1984).
Takeuchi, "An application of tetrazolium (MTT) colorimetric assay for the screening of anti–herpes simplex virus compounds," *J. of virological Methods* 33:61–71 (1991).

* cited by examiner

Primary Examiner—Christopher S. F. Low
Assistant Examiner—Abdel A. Mohamed
(74) Attorney, Agent, or Firm—Brown Martin Haller & McClain LLP

(57) ABSTRACT

The present invention provides a compound having the structure:

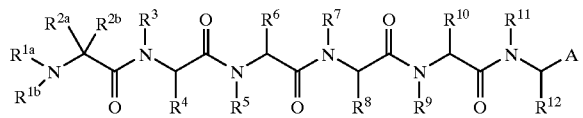

wherein $R^{1a}$ and $R^{1b}$ are independently selected from the group consisting of —H, alkyl, lower-alkyl, substituted alkyl and substituted lower-alkyl;

$R^{2a}$ and $R^{2b}$ are independently selected from the group consisting of —H, lower-alkyl, and substituted lower-alkyl;

$R^3$ is —H, lower-alkyl, substituted lower-alkyl and where $R^3$ and $R^4$ are attached together by a lower-alkyl or a substituted lower-alkyl moiety;

$R^4$ is —H, lower-alkyl, substituted lower-alkyl and where $R^3$ and $R^4$ are attached together form a lower-alkyl or substituted lower-alkyl bridge;

$R^5$, $R^7$, $R^9$ and $R^{11}$ are independently selected from the group consisting of —H, lower-alkyl, and substituted lower-alkyl;

$R^6$ is —H, lower-alkyl and substituted lower-alkyl;

$R^8$ is —H, lower-alkyl and substituted lower-alkyl;

$R^{10}$ is —H, lower-alkyl and substituted lower-alkyl;

$R^{12}$ is —H, lower-alkyl and substituted lower-alkyl; and

A is —C(O)—$R^{13}$, wherein $R^{13}$ is —H, —OH, alkyl, lower-alkyl, substituted lower-alkyl or —O(lower-alkyl); —CH$_2$—OR$^{14}$ wherein $R^{14}$ is —H, —C(O)CH$_3$, alkyl, lower-alkyl or substituted lower-alkyl; or —CH$_2$—NR$^{15}$R$^{16}$, where $R^{15}$ and $R^{16}$ are independently selected from —H, lower-alkyl, alkyl, substituted lower-alkyl or substituted alkyl;

a pharmaceutically acceptable salt or derivatives thereof, useful for preventing or treating viral and microbial infections.

26 Claims, No Drawings

```
                         SEQUENCE LISTING

<160> NUMBER OF SEQ ID NOS: 1

<210> SEQ ID NO 1
<211> LENGTH: 6
<212> TYPE: PRT
<213> ORGANISM: Scytalidium CNL240
<220> FEATURE:
<221> NAME/KEY: MOD_RES
<222> LOCATION: (1)
<223> OTHER INFORMATION: Aib;
<220> FEATURE:
<221> NAME/KEY: MOD_RES
<222> LOCATION: (6)
<223> OTHER INFORMATION: leucinol

<400> SEQUENCE: 1

Xaa Pro Leu Val Gln Xaa
  1               5
```

HALOVIR, AN ANTIVIRAL MARINE NATURAL PRODUCT, AND DERIVATIVES THEREOF

This invention was made with government support under grant NA36RG0537 awarded by the National Oceanic and Atmospherics Administration and the National Cancer Institute under grant CA 44848. The government has certain rights in the invention.

BACKGROUND OF THE INVENTION

1. Field of the Invention

This invention relates generally to the fields of biochemistry and medicine, and more specifically to compounds useful as antiviral and antimicrobial agents.

2. Background Information

Viral infections have long been and continue to be a major cause of human suffering. The large variety of viruses combined with the diverse types of afflictions continue to challenge endeavors to find and make available agents capable of treating or mitigating the effects viral infections.

One family of viruses that is particularly troublesome is the Herpes simplex viruses (HSV). HSV is a relatively common human pathogen which can cause fatal disease in the young or immunocompromised. HSV includes two closely related variants designated type 1 ("HSV-1") and type 2 ("HSV-2"). These types cross react strongly, but can be distinguished by neutralization titrations. HSV-1 and HSV-2 are responsible for a variety of human diseases, such as skin infection, fever blisters, genital herpes, viral encephalitis, and the like. Both HSV-1 and HSV-2 have been shown to be capable of causing neonatal infections. HSV-2 genital infections has been linked with the development of cervical cancer.

Cytomegalovirus (CMV) is another member of the HSV family. CMV infection is the leading cause of congenital viral infections with an incidence averaging 1% of all live births. An additional 5% to 10% of infants acquire CMV perinatally as a result of mother-to-infant transmission. Although the virus is widely distributed in the population about 40% of women enter pregnancy without antibodies and thus are susceptable to infection. CMV infections of the eye have resulted in the loss of sight to immunocomprised individuals afficted with AIDS. CMV infection is also a major concern organ transplant recipients, especially, kidney and liver transplants.

A major avenue for HSV transmission is through skin to skin contact with an infected area, such as genital to genital contact, and contact to the eye with the hands. It is therefore desirable to administer a potent antiviral, particularly, anti-HSV or anti-CMV agent topically prior to potential viral introduction into an individual.

Because of these disease conditions, there is a continuing effort made by individual academic investigators, and by small and large pharmaceutical companies to identify new and useful antiviral agents. Various drug discovery strategies have been developed. In some instances, derivatives of known effective drugs are prepared and examined for improved or different, but useful, characteristics. Another approach is to develop or acquire large libraries of randomly synthesized drugs candidates, and screen these compounds for potential efficacy as antiviral agents. Both of these methods have resulted in the identification of potentially useful antiviral agents. Yet another approach has been to identify potentially useful drugs that are produced naturally by living organisms. For example, paclitaxel is a chemical that is produced by the yew tree and, when purified, is effective in treating cancers such as ovarian carcinoma. Applying a similar discovery strategy, naturally occurring agents with antiviral activity are being sought and screened for antiviral activity.

A naturally occurring compound has been recently discovered, which surprisingly possesses antiviral activity, and fulfills the needs of the requirements for an antiviral agent.

SUMMARY OF THE INVENTION

The present invention provides a compound having the structure:

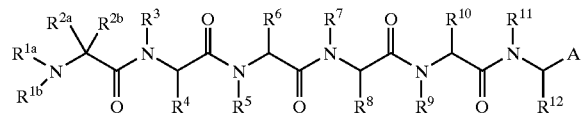

wherein, $R^{1a}$ and $R^{1b}$ are independently selected from the group consisting of —H, alkyl, lower-alkyl, substituted alkyl and substituted lower-alkyl;

$R^{2a}$ and $R^{2b}$ are independently selected from the group consisting of —H, lower-alkyl, and substituted lower-alkyl;

$R^3$ is —H, lower-alkyl, substituted lower-alkyl and where $R^3$ and $R^4$ are attached together by a lower-alkyl or a substituted lower-alkyl moiety;

$R^4$ is —H, lower-alkyl, substituted lower-alkyl and where $R^3$ and $R^4$ are attached together form a lower-alkyl or substituted lower-alkyl bridge;

$R^5$, $R^7$, $R^9$ and $R^{11}$ are independently selected from the group consisting of —H, lower-alkyl, and substituted lower-alkyl;

$R^6$ is —H, lower-alkyl and substituted lower-alkyl;

$R^8$ is —H, lower-alkyl and substituted lower-alkyl;

$R^{10}$ is —H, lower-alkyl and substituted lower-alkyl;

$R^{12}$ is —H, lower-alkyl and substituted lower-alkyl; and

A is —C(O)—$R^{13}$, wherein $R^{13}$ is —H, —OH, alkyl, lower-alkyl, substituted lower-alkyl or —O(lower-alkyl); —$CH_2$—$OR^{14}$ wherein $R^{14}$ is —H, —C(O)$CH_3$, alkyl, lower-alkyl or substituted lower-alkyl; or —$CH_2$—$NR^{15}R^{16}$, where $R^{15}$ and $R^{16}$ are independently selected from —H, lower-alkyl, alkyl, substituted lower-alkyl or substituted alkyl;

a pharmaceutically acceptable salt or derivatives thereof, useful for preventing and treating viral and microbial infections.

DETAILED DESCRIPTION OF THE INVENTION

The present invention provides method for treating viral infections, in particular, herpes simplex type I and II viral infections and cytomegalovirus.

The present invention provides a compound having the structure:

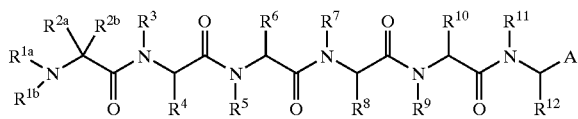

wherein,
- $R^{1a}$ and $R^{1b}$ are independently selected from the group consisting of —H, alkyl, lower-alkyl, substituted alkyl and substituted lower-alkyl;
- $R^{2a}$ and $R^{2b}$ are independently selected from the group consisting of —H, lower-alkyl, and substituted lower-alkyl;
- $R^3$ is —H, lower-alkyl, substituted lower-alkyl and where $R^3$ and $R^4$ are attached together by a lower-alkyl or a substituted lower-alkyl moiety;
- $R^4$ is —H, lower-alkyl, substituted lower-alkyl and where $R^3$ and $R^4$ are attached together form a lower-alkyl or substituted lower-alkyl bridge;
- $R^5$, $R^7$, $R^9$ and $R^{11}$ are independently selected from the group consisting of —H, lower-alkyl, and substituted lower-alkyl;
- $R^6$ is —H, lower-alkyl and substituted lower-alkyl;
- $R^8$ is —H, lower-alkyl and substituted lower-alkyl;
- $R^{10}$ is —H, lower-alkyl and substituted lower-alkyl;
- $R^{12}$ is —H, lower-alkyl and substituted lower-alkyl; and
- A is —C(O)—$R^{13}$, wherein $R^{13}$ is —H, —OH, alkyl, lower-alkyl, substituted lower-alkyl or —O(lower-alkyl); —$CH_2$—$OR^{14}$ wherein $R^{14}$ is —H, —C(O) $CH_3$, alkyl, lower-alkyl or substituted lower-alkyl; or —$CH_2$—$NR^{15}R^{16}$, where $R^{15}$ and $R^{16}$ are independently selected from —H, lower-alkyl, alkyl, substituted lower-alkyl or substituted alkyl;

a pharmaceutically acceptable salt or derivatives thereof, useful for preventing and treating viral and microbial infections.

The invention provides a method for preventing and treating viral infections, such as, HSV-1, HSV-2 and CMV.

In addition, the invention provides a method for preventing and treating microbial infections.

Further, the invention provides a method of treating viral infections in combination with antiviral agents, such as, acyclovir, penciclovir, valaciclovir, famciclovir, ganciclovir and foscarnet.

Still further, the invention provides a method of preventing and treating,viral infection in combination with antiviral topical agents, such as, nonoxynol.

Definitions

As used herein the term "alkyl" refers to a branched or straight chain monovalent saturated aliphatic hydrocarbon radical of seven to twenty carbon atoms. This term is further exemplified by such radicals as n-heptyl, n-decyl, n-tridecyl and the like.

As used herein, the term "lower-alkyl" refers to a branched or straight chain monovalent alkyl radical of one to six carbon atoms. This term is further exemplified by such radicals as methyl, ethyl, propyl, isopropyl, butyl (for example, isobutyl, t-butyl, or n-butyl), pentyl (for example, 2-methylbutyl, 3-methylbutyl), and hexyl (for example, 2-methylpentyl, 2,2-dimethylbutyl and 2,3-dimethylbutyl).

As used herein, the term "substituted alkyl" refers to an alkyl moiety optionally substituted with hydroxy, carbonyl, carboxy, halide, amidyl, guanidyl, thio and carboxyamide. Example of substituted alkyl moieties, include but are not limited by, tetradecanoyl, nonylcarbonyl, and 1-chloropentylcarbonyl.

As used herein the term "substituted lower-alkyl" refers to a lower-alkyl moiety optionally substituted with hydroxy, carbonyl, carboxy, halide, amidyl, guanidyl, thio, and carboxyamide. Examples of substituted lower-alkyl moieties, include but are not limited by, methoxycarbonyl, 4-aminobutyl, and 4-guanidylpropyl.

As used herein, the term "lower-alkyl bridge" or "substituted lower-alkyl bridge" refers to a lower-alkyl moiety optionally substituted with hydroxy, carbonyl, carboxy, halide, acidyl, linked such that it forms a moiety within the peptide backbone of the compound. For example where $R^3$ and $R^4$ together are linked by a propyl group, the resultant lower-alkyl bridge with $R_3$ and $R_4$ forms the cyclopentyl functional group of proline; or where $R^3$ and $R^4$ together form a 2-hydroxypropyl group, the resultant lower-alkyl bridge with $R_3$ and $R_4$ forms the hydroxycyclopentyl functional group of hydroxyproline.

As used herein, the following terms refer to the corresponding organic moieties,
"carboxyl" refers to "—C(O)O—";
"acetyl" or "Ac" refers to "$CH_3$—C(O)—"; and
"acetoxy" or "AcO" refers to "$CH_3$—C(O)—O—."

As used herein, the term "isolated" or "substantially pure" means that the compound of the invention is at least about 50% free of materials with which it normally is associated in a cell, particularly CNL240, and generally is about 90% or 95% free of such materials, particularly at least 99% free of such material.

As used herein, the term "salt" or "pharmaceutically-acceptable salt" encompasses those salts that form with the carboxylate anions and includes salts formed with the organic and inorganic cations such as those chosen from the alkali and alkaline earth metals, (for example, lithium, sodium, potassium, magnesium, barium and calcium); ammonium ion; and the organic cations (for example, dibenzylammonium, benzylammonium, 2-hydroxyethylammonium, bis(2-hydroxyethyl)ammonium, phenylethylbenzylammonium, dibenzylethylenediammonium, and like cations.) Other cations encompassed by the above term include the protonated form of procaine, quinine and N-methylglucosamine, the protonated forms of basic amino acids such as glycine, ornithine, histidine, phenylglycine, lysine, and arginine. Furthermore, any zwitterionic form of the instant compounds formed by a carboxylic acid and an amino group is referred to by this term. A preferred cation for the carboxylate anion is the sodium cation. Further included are salts that form by standard acid-base reactions with basic groups (such as amino groups), including organic or inorganic acids. Such acids include hydrochloric, sulfuric, phosphoric, acetic, succinic, citric, lactic, maleic, fumaric, palmitic, cholic, palmodic, mucic, D-glutamic, D-camphoric, glutaric, phthalic, tartaric, lauric, stearic, salicylic, methane sulfonic, benzenesulfonic, sorbic, picric,;benzoic, cinnamic acids, and the like.

The compounds of the above structure may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

As used herein, the term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, benzyl, allyl, 4,4',4"-trimethoxytrityl, trimethylsilyl, (t-butyl)

dimethylsilyl, 2,2,2-trichloroethoxycarbonyl, and the like. Further examples of hydroxy-protecting groups are described by Reese and Haslam, "Protective Groups in Organic Chemistry" (McOmie, Ed., Plenum Press, New York, N.Y., 1973), Chaps. 3 and 4; and Greene and Wuts, "Protective Groups in Organic Synthesis," Second Edition (John Wiley and Sons, New York, 1991), Chaps. 2 and 3; each of which is incorporated herein by reference. A preferred hydroxy-protecting group is the tert-butyl group. The related term "protected hydroxy" denotes a hydroxy group bonded to one of the above hydroxy-protecting groups.

As used herein, the term "amino-protecting group" as used herein refers to substituents of the amino group commonly employed to block or protect the amino functionality while reacting other functional groups of the molecule. The term "protected (monosubstituted)-amino" means there is an amino-protecting group on the monosubstituted amino nitrogen atom. Examples of such amino-protecting groups include the formyl group, the trityl group, the phthalimido group, the trichloroacetyl group, the trifluoroacetyl group, the chloroacetyl, bromoacetyl, and ibdoacetyl groups, urethane-type protecting groups, such as t-butoxycarbonyl ("Boc"), 2-(4-biphenylyl)propyl-2-oxycarbonyl, 2-phenylpropyl-2-oxycarbonyl, 2-(4-xenyl) isopropoxycarbonyl, 1,1-diphenylethyl-1-oxycarbonyl, 1,1-diphenylpropyl-1-oxycarbonyl, 2-(3,5-dimethoxyphenyl) propyl-2-oxycarbonyl, 2-(p-toluyl) propyl-2-oxycarbonyl, cyclopentanyloxycarbonyl, 1-methylcyclopentanyl-oxycarbonyl, cyclohexanyloxycarbonyl, 1-methyl-cyclohexanyloxycarbonyl, 2-methylcyclohexanyl-oxycarbonyl, 2-(4-toluylsulfonyl) ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxycarbonyl, 4-methoxybenzyloxycarbonyl, α2,4,5,-tetramethylbenzyl-oxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlrobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy) benzyloxycarbonyl and the like; the benzoylmethylsulfonyl group, the 2,2,5,7,8-pentamethylchroman-6-sulfonyl group, the dithiasuccinoyl group, the 2-(nitro)phenyl-sulfenyl group, the diphenylphosphine oxide group, and like amino-protecting groups. The species of amino-protecting group employed are not critical so long as the derivatized amino group is stable to the conditions of the subsequent reaction (s) and can be removed at the appropriate point without disrupting the remainder of the molecule. Preferred amino-protecting groups are Boc, Cbz and Fmoc. Further examples of amino-protecting groups embraced by the above term are well known in organic synthesis and the peptide art and are described, for example, by Greene and Wuts, supra, 1991, Chap. 7; Bodanzsky, "Principles of Peptide Synthesis," St. and 2nd revised Ed. (Springer-Verlag, New York, 1984 and 1993); Stewart and Young, "Solid Phase Peptide Synthesis," 2nd Ed. (Pierce Chemical Co., Rockford Ill., 1984); Atherton and Shephard, "Solid Phase Peptide Synthesis—A Practical Approach" (IRL Press, Oxford England, 1989), each of which is incorporated herein by reference. The related term "protected amino" defines an amino group substituted with an amino-protecting group discussed above.

As used herein, the term "amino acid" refers to an organic chemical compound or moiety that contains both a basic amino group and an acidic carboxylic group. Alpha amino acids are where the amino group is attached to the alpha carbon. Amino acids are the primary structural units of peptides and proteins. Amino acids can be classified into three classes based on the charge status of the R group, that is, apolar R, uncharged polar R, charged R, as listed below the twenty most common naturally occurring amino acids.

| Amino Acid | Radical | Abbreviations | |
|---|---|---|---|
| | | 3-Letter | 1-Letter |
| Amino Acids-Apolar R Groups | | | |
| alanine | methyl | ala | A |
| valine | 2-propyl | val | V |
| leucine | 2-methylpropyl | leu | L |
| isoleucine | 2-butyl | ile | I |
| proline | propyl group-cyclize between α-amino and α-carbon | pro | P |
| phenylalanine | benzyl | phe | F |
| trytophan | 3-indolylmethyl | tyr | W |
| methionine | methylthioethyl | met | M |
| Amino Acids-Uncharged Polar R Group | | | |
| glycine | H | gly | G |
| serine | hydroxymethyl | ser | S |
| threonine | 1-hydroxyethyl | thr | T |
| cysteine | thiolmethyl | cys | C |
| tyrosine | 4-hydroxyphehylmethyl | tyr | Y |
| asparagine | aminocarbonylmethyl | asn | N |
| glutamine | 3'-propionyl acid amide | gln | Q |
| Amino Acids-Charged R Groups | | | |
| aspartic acid | carboxymethyl | asp | D |
| glutamic acid | carboxyethyl | glu | E |
| lysine | 4-aminobutyl | lys | K |
| arginine | 3-guanylpropyl | arg | R |
| histidine | 4-imidazoylmethyl | his | H |

Alternatively, amino acids can be classified according to their acid/base characteristics, that is, neutral, basic or acidic.

As used herein, the term "Aib" refers to the amino acid 2-aminoisobutyric acid, which has the corresponding structure,

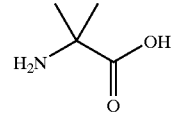

As used herein, the term "Leu(OH)" refers to the structure,

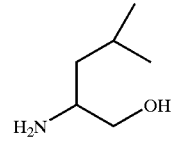

As used herein, the "derivative" of a polypeptide or protein refers to a polypeptide or protein where its amino acid sequence is altered by one or more amino acids. The derivative may have "conservative" changes, wherein a substituted amino acid has similar structural or chemical properties, e.g., substitution of an apolar amino acid with another apolar amino acid (such as replacement of leucine with isoleucine). The derivative may also have "nonconservative" changes, wherein a substituted amino acid has different but sufficiently similar structural or chemical properties that permits such a substitution without adversely effecting the desired biological activity, e.g., replacement of an amino acid with an uncharged polar R group with an amino acid with an apolar R group (such as replacement of glycine with tryptophan), or alternatively replacement of an amino acid with a charged R group with an amino acid with an uncharged polar R group (such as replacement of lysine with asparagine).

Similar minor modifications may also include amino acids deletions or insertions or both. Guidance in, determining which amino acid residues may be modified as indicated above without abolishing the desired biological functionality may be determined using computer programs well known in the art, for example, DNASTAR software. In addition, the derivative may also result from chemical modifications to the encoded polypeptlide, including but not limited to the following, replacement of hydrogen by an alkyl, acyl, or amino group; esterification of a carboxyl group with a suitable-alkyl or aryl moiety; alkylation of a hydroxyl group to form an ether derivative. Further a derivative may also result from the substitution of a L-configuration amino acid with its corresponding D-configuration counterpart. Another strategy for derivatizing peptides, polypeptides and proteins is to alter the structure of specific amino acids. For example, the carboxy moiety can be reduced to hydroxy group, such as in the conversion of leucinol for leucine; where an additional methyl group can be substituted to the α-carbon atom, such as in the conversion of alanine to aminoisobutyric acid; or where a hydroxy group is substituted to the 4 position of proline resulting in the conversion of proline to 4-hydroproline.

As used herein, the term "mimetic" refers to a molecule, the structure of which has conformational similarity to the structure of a protein/polypeptide or portions thereof and, as such, is able to effect some or all of the actions of the peptide, polypeptide or protein.

Depending on the choice of solvent and other conditions known to the practitioner skilled in the art, compounds of this invention may also take the ketal or acetal form, which forms are included in the instant invention. In addition, it should be understood that the equilibrium forms of the compounds of this invention may include tautomeric forms. All such forms of these compounds are expressly included in the present invention.

The compounds of the invention can be modified by appropriate functionalities to enhance selective biological properties. Such modifications are known in the art and include those which increase biological penetration into a given biological system, for example, blood, the lymphatic system, or the central nervous system, increase oral availability, increase solubility to allow administration by injection, alter metabolism and alter rate of exertion. In addition, the compounds can be altered to a pro-drug form such that the desired compound is created in the body of the patient as the result of the action of metabolic or other biochemical processes on the pro-drug. Some examples of pro-drug forms include ketal, acetal, oxime, and hydrazone forms of compounds which contain ketone or aldehyde groups.

One of ordinary skill in the art will recognize that the compounds of the present invention can be described and named following accepted nomenclature for peptides. The stereoconfiguration of the α-carbon of a residue is indicated by the letters L or D preceding the three-letter code for the residue. Graphically, the stereoconfiguration about a chiral center is designated by either a solid or hatched wedge shaped bonds. For the textual convention, the absence of a letter or the presence of both letters indicates a mixture of the L and D isomers, or that diastereomers were separated but not identified. In a similar manner, the presence of a non-wedged bond indicates a mixture of the L and D isomers, or that diastereomers were separated but not identified.

Some representative compounds are named in the following examples.

For example, Halovir A can be depicted by following structure, wherein, $R^{1a}$ is tetradecanoyl;, $R^{1b}$ is —H;

$R^{2a}$ and $R^{2b}$ are methyl;

$R^3$ and $R^4$ are attached together by 2-hydroxypropyl;

$R^5$, $R^7$, $R^9$ and $R^{11}$ are H;

$R^6$ and $R^{12}$ are 2-methylpropyl;

$R^8$ is 2-propyl;

$R^{10}$ is 3'-propionyl acid amide; and

A is —CH$_2$—OR$^{14}$ where $R^{14}$ is H;

as well as by, CH$_3$(CH$_2$)$_{12}$C(O)-Aib-Hyp-Leu-Val-Gln-Leu (OH), with the corresponding specific structure, For example, Halovir B can be depicted by following structure, wherein, $R^{1a}$ is tetradecanoyl;

$R^{1b}$ is —H;

$R^{2a}$ and $R^{2b}$ are methyl;

$R^3$ and $R^4$ are attached together by 2-hydroxypropyl;

$R^5$, $R^7$, $R^9$ and $R^{11}$ are H;

$R^6$ and $R^{12}$ are 2-methylpropyl;

$R^8$ is methyl;

$R^{10}$ is 3'-propionyl acid amide; and

A is —CH$_2$—OR$^{14}$ where $R^{14}$ is H;

as well as by, CH$_3$(CH$_2$)$_{12}$C(O)-Aib-Hyp-Leu-Ala-Gln-Leu (OH) with the corresponding specific structure,

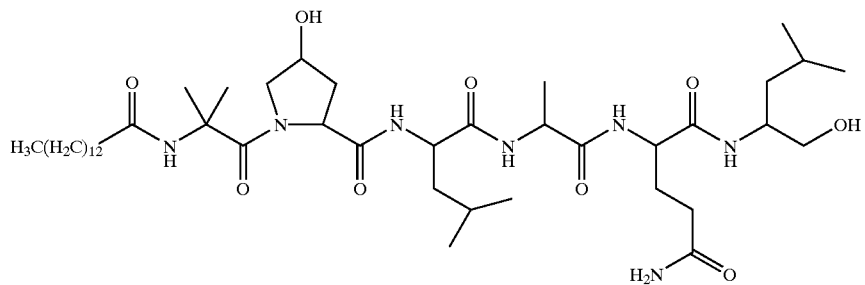

For example, Halovir C can be depicted by the structure,

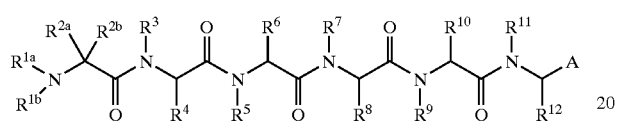

wherein,
$R^{1a}$ is tetradecanoyl;
$R^{1b}$ is —H;
$R^{2a}$ and $R^{2b}$ are methyl;
$R^3$ and $R^4$ are attached together by propyl;
$R^5$, $R^7$, $R^9$ and $R^{11}$ are H;
$R^6$ and $R^{12}$ are 2-methylpropyl;
$R^8$ is 2-propyl;
$R^{10}$ is 3'-propionyl acid amide; and
A is —CH$_2$—OR$^{14}$ where $R^{14}$ is H;
as well as, CH$_3$(CH$_2$)$_{12}$C(O)-Aib-Pro-Leu-Val-Gln-Leu(OH) (SEQ. ID. NO.: 1), with the corresponding specific structure,

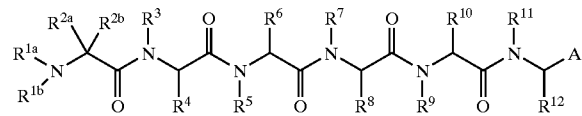

wherein,
$R^{1a}$ is tetradecanoyl;
$R^{1b}$ is —H;
$R^{2a}$ and $R^{2b}$ are methyl;
$R^3$ and $R^4$ are attached together by 2-acetoxypropyl;
$R^5$, $R^7$, $R^9$ and $R^{11}$ are H;
$R^6$ and $R^{12}$ are 2-methylpropyl;
$R^8$ is 2-propyl;
$R^{10}$ is 3'-propionyl acid amide; and
A is —CH$_2$-OAc;

For example, Halovir D can be depicted by the following structure,

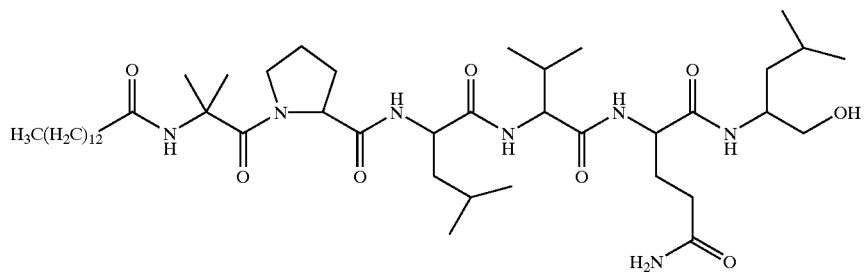

as well as, CH$_3$(CH$_2$)$_{12}$C(O)-Aib-Hyp(OAc)-Leu-Val-Gln-Leu(OAc), with the corresponding specific structure,

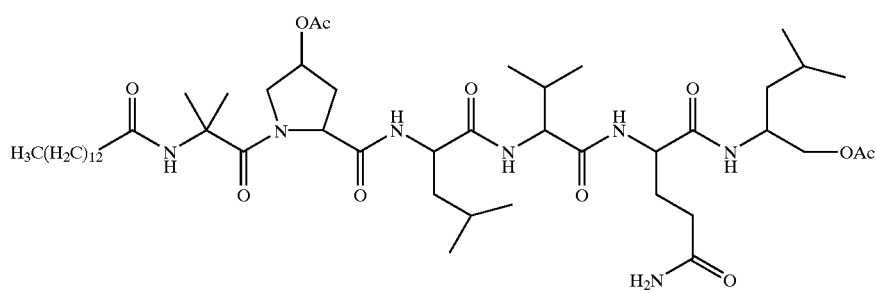

For example, Halovir E can be depicted by the following structure,

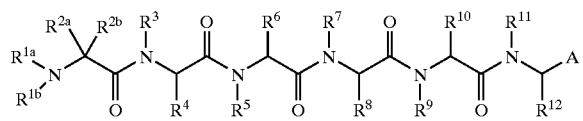

wherein, $R^{1a}$ is tetradecanoyl;

$R^{1b}$ is —H;

$R^{2a}$ and $R^{2b}$ are methyl;

$R^3$ and $R^4$ are attached together by 2-hydroxypropyl;

$R^5$, $R^7$, $R^9$ and $R^{11}$ are H;

$R^6$ and $R^{12}$ are 2-methylpropyl;

$R^8$ is methyl;

$R^{10}$ is 3'-propionyl acid amide; and

A is —C(O)OCH$_3$;

as well as, CH$_3$(CH$_2$)$_{12}$C(O)-Aib-Hyp-Leu-Val-Gln-Leu-OMe), with the corresponding specific structure,

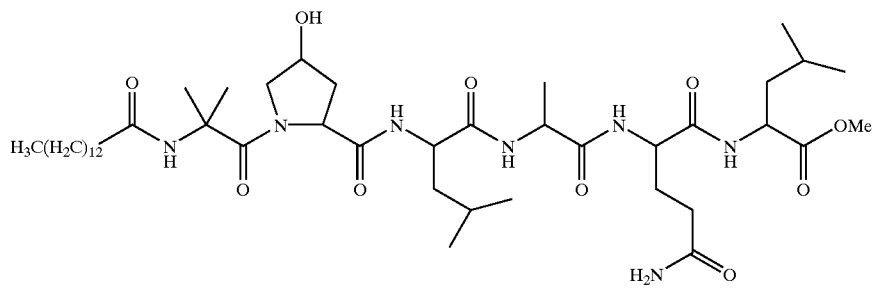

As used herein, the term "halovir" refers to a family of hexapeptides and hexapeptide like compounds isolated from the fermentation of the marine fungus Scytalidium sp. CNL240 from a sample of the seagrass *Halodule wrightii* collected from the Bahamas. The marine fungus has been deposited with the American Type Culture Collection ATCC Designation No. 74470 (Manassas, Va.).

The present invention includes substantially purified compounds isolated from the fermentation of the marine fungus, Scytalidium sp. CNL240 and also includes derivatives of halovir. In addition to availability from a natural source, halovirs can be synthesized using conventional techniques as disclosed herein (see Examples 2 and 3). Advantageously, these compounds are conveniently synthesized from readily available starting materials. As disclosed herein, compounds of the invention, halovirs A to C, can also be isolated in substantially purified form from Scytalidium sp. CNL240 and then can be chemically modified as desired to obtain derivative of the original compounds, such as Halovir D and Halovir E, to add one or more of the substituents discussed above. In steps calling for natural seawater, artificial formulas can be used as a substitute. As used herein, the term "isolated" or "substantially purified" means that the compound of the invention is at least about 50% free of materials with which it normally is associated in a cell, particularly Scytalidium sp. CNL240 and generally is about 90% or 95% free of such materials, particularly at least 99% free of such material.

If desired, a compound of the invention can be in the form of a pharmaceutical composition, comprising the compound or a salt thereof, and pharmaceutically acceptable excipient(s). As used herein, the terms "pharmaceutically acceptable" and "physiologically acceptable" are intended to have the same meaning. Pharmaceutically acceptable excipients, which can be an adjuvant or other vehicle, include, but are not limited to, ion exchange resins, alumina, aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene-polyoxypropylene-block polymers, polyethylene glycol and wool fat, and the like.

A compound of the invention, when administered to a subject such as a mammalian subject, for example, a human, can be administered orally, parenterally, by inhalation, topically, rectally, nasally, buccally or vaginally, and can be contained in an implanted reservoir. Parenteral administration can be by subcutaneous, intracutaneous, intravenous, intramuscular, intra-articular, intrasynovial, intrasternal, intrathecal, intralesional or intracranial injection or by an infusion method.

A compound of the invention, which can comprise a pharmaceutical composition, can be in the form of a sterile injectable preparation, for example, a sterile injectable aqueous or oleaginous suspension. Such a suspension can be formulated by methods known in the art using, for example, suitable dispersing or wetting agents such as Tween 80, or suspending agents. The sterile injectable preparation also can be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic saline solution. In addition, sterile, fixed oils are conventionally employed as a solvent or suspending medium. For this purpose, any bland fixed oil can be employed, including synthetic monoglycerides or diglycerides. Fatty acids such as oleic acid and its glyceride derivatives also are useful in the preparation of injectables, as are natural pharmaceutically acceptable oils such as olive oil or castor oil, especially in their polyoxyethylated versions. These oil solutions or suspensions also can contain a long chain alcohol diluent or dispersant.

A compound of the invention can be orally administered in any orally acceptable dosage form including, but not limited to, capsules, tablets and aqueous suspensions and solutions. In the case of tablets for oral use, carriers that commonly are used include lactose and corn starch. Lubricating agents such as magnesium stearate also can be added. For oral administration in capsule form, useful diluents include lactose and dried corn starch. When aqueous suspensions are administered orally, the active ingredient can be combined with emulsifying and suspending agents. If desired, certain sweetening, flavoring or coloring agents can be added.

A compound of the invention also can be formulated in a pharmaceutical composition for administration in the form of suppositories for rectal administration. Such a composition can be prepared by mixing a compound of the invention, for example, halovir, with a suitable non-irritating excipient that is solid at room temperature, but liquid at the rectal temperature. Such materials include, but are not limited to, cocoa butter, beeswax and polyethylene glycols.

Topical administration of a compound of the invention can be particularly useful when the desired treatment involves areas or organs readily accessible to topical application. For application topically to the skin, for example, the compound should be formulated with a suitable ointment containing the active compound suspended or dissolved in a carrier, or can be in the form of a spray. Carriers for topical administration of the compounds of the invention include, but are not limited to, mineral oil, liquid petroleum, white petroleum, propylene glycol, polyoxyethylene, polyoxypropylene compound, emulsifying wax and water. A compound of the invention also can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. A compound also can be formulated to allow topical application to the lower intestinal tract by rectal suppository formulation or in a suitable enema formulation. Topically applied transdermal patches and eye drop formulations containing a compound of the invention are also included in this invention.

A compound of the invention also can be administered by nasal aerosol or inhalation. Such compositions are prepared according to techniques well known in the art of pharmaceutical formulation and can be prepared as solutions in saline, employing benzyl alcohol or other suitable preservatives, absorption promoters to enhance bioavailability, fluorocarbons, or other solubilizing or dispersing agents.

A compound of the invention can be advantageously administered with other antiviral agents, such as, acyclovir, penciclovir, valaciclovir, famciclovir, ganciclovir and foscarnet. Further the invention can be further administered in combination the antiviral agents listed above with other topical antiviral agents, such as nonoxynol or the like. A pharmaceutical composition of matter comprising such a combination would possess the advantage of being able to address the viral infection along diverse but yet effective avenues as provided by the beneficial characteristics of the individual components of the combination, thus allowing for a great collective syngergistic benefit to the afflicted subject.

EXAMPLES

The following examples are given to enable those skilled in the art to more clearly understand and to practice the present invention. They should not be considered as limiting the scope of the invention, but merely as being illustrative and representative thereof.

Example 1

Production of Halovirs

The halovirs were produced by a marine fungus designated strain CNL240 isolated from a sample of the seagrass *Halodule wrightii* collected in the Bahamas. The seagrass sample was air dried and dissected into small pieces. The pieces were placed onto a seawater based agar medium containing the antibiotics penicillin G and streptomycin sulfate to reduce bacterial growth. Following incubation, fungal hyphae were observed growing away from the sample and out onto the agar medium. A small piece of this growth was removed with a sterile scalpel and transferred to a fresh plate containing the agar medium. Following the development of adequate growth on this new plate, small pieces of the mycelium were cut away, placed in sterile vials containing the growth medium enriched with 10% glycerol, and cryopreserved at −80° C. Strain CNL240 was identified as the marine fungus Scytalidium sp. using the results of fatty acid analysis as applied to a fungal similarity index, i.e., an index identifying a particular fungus by the type of fatty acids produced also known as the similarity index, (James H. Graham, Fatty Acid Methyl Ester Profiles. for Characterization of Glomalean Fungi and Their Endomycorrhizae, Applied and Environmental Microbiology, January 1995, p. 58–64). The similarity index for this genus was 0.807.

For production of the halovirs, 10 ml of the marine-based medium YPG consisting of 1% glucose, 0.5% yeast extract, 0.5% peptone, 100% seawater was inoculated with CNL240. After 5 days of static growth under ambient temperature and lighting conditions, the culture was transferred to 1 L of the same medium. The 1 L culture was allowed to grow for 21 days without shaking at 27° C. Following fermentation, the mycelium was filtered away from the broth, freeze-dried, and extracted with 1:1 methanol:dichloromethane. The resulting extract was concentrated under vacuum yielding a crude mycelial extract.

Example 2

Isolation of Halovir A, B and C

The crude mycelial extract was fractionated by high speed counter-current chromatography using a solvent system composed of 10% hexanes, 30% ethyl acetate, 30% methanol, and 30% water. The upper layer of the biphasic system was used as the mobile phase. Five fractions were generated. The fractions were assayed for antiviral activity using an MTT assay for HSV-1 activity as described in Example 6. Fraction three was found to have the highest antiviral activity. This fraction was subjected to C18 flash chromatography using a gradient of 10% to 0% water in methanol. New fractions were taken and assayed for antiviral activity. The third and fourth fractions were found to have strong antiviral activity. C18 HPLC of these fractions using 7% water in methanol yielded three pure compounds that displayed potent antiviral activity against HSV-1. These compounds were designated Halovir A, Halovir B and Halovir C. Their structures were elucidated by combined mass spectrometry, and proton and carbon NMR analysis.

Halovir A
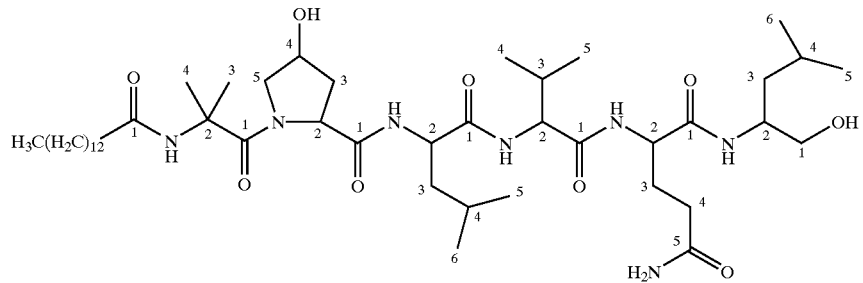
| | C# | δ¹³C | DEPT | δ¹H (mult, J (Hz)) |
|---|---|---|---|---|
| Leucinol | 1 | 66.0 | CH₂ | 4.04(m) |
| | 2 | 50.8 | CH | 4.62(m) |
| | 3 | 41.2 | CH₂ | 1.94(m), 1.76(m) |
| | 4 | 25.6 | CH | 1.9(m) |
| | 5 | 24.3 | CH₃ | 0.98(d, 6.3) |
| | 6 | 22.8 | CH₃ | 0.98(d, 6.3) |
| | NH | | | 7.76(d, 9.3) |
| | OH | | | 5.83 |
| Glutamine | 1 | 172.8 | | |
| | 2 | 55.4 | CH | 5.05(m) |
| | 3 | 29.4 | CH₂ | 2.9(m), 2.6(m) |
| | 4 | 33.8 | CH₂ | 2.9(m), 2.6(m) |
| | 5 | 175.5 | | |
| | NH₂ | | | 8.09(s), 7.57(s) |
| | NH | | | 8.12(d, 7.3) |
| Valine | 1 | 172.8 | | |
| | 2 | 61.9 | CH | 4.67(m) |
| | 3 | 30.3 | CH | 2.68(m) |
| | 4 | 19.6 | CH₃ | 1.30(d, 6.8) |
| | 5 | 20.1 | CH₃ | 1.21(d, 6.8) |
| | NH | | | 8.12(d, 7.3) |
| Leucine | 1 | 175.8 | | |
| | 2 | 55.4 | CH | 4.67(m) |
| | 3 | 40.3 | CH₂ | 2.33(m), 2.06(m) |
| | 4 | 26.0 | CH | 2.05(m) |
| | 5 | 24.1 | CH₃ | 1.14(d, 5.86) |
| | 6 | 21.6 | CH₃ | 1.02(d, 5.86) |
| | NH | | | 8.62(d, 6.35) |
| Hydroxyproline | 1 | 175.4 | | |
| | 2 | 63.3 | CH | 5.25(dd, 9.8, 8.0) |
| | 3 | 38.4 | CH₂ | 2.72(dd, 8.0, 13) |
| | | | | 2.08(dd, 10, 13) |
| | 4 | 70.9 | CH | 4.75(m) |
| | 5 | 58.2 | CH₂ | 4.34(d, 11.2) |
| | | | | 3.81(dd, 11.2, 2.5) |
| | OH | | | 6.99(d, 2.5) |
| Aib | 1 | 175.1 | | |
| | 2 | 57.3 | | |
| | 3 | 27.21 | CH₃ | 1.80(s) |
| | 4 | 24.4 | CH₃ | 1.60(s) |
| | NH | | | 9.60(s) |
| Tetradecanoyl chain | 1 | 174.7 | | |
| | 2 | 36.3 | CH₂ | 2.56(m) |
| | 3 | 26.4 | CH₂ | 1.77(m) |
| | 4 | 32.6 | CH₂ | 1.25(m) |
| | 5–12 | 30 | CH₂ | 1.2(m) |
| | 13 | 23.4 | CH₂ | 1.25(m) |
| | 14 | 14.8 | CH₃ | 0.88(t) |
HRFABMS $[M+Na]^+$ m/z 888.6119; $[\alpha]_D$ −13° (c 0.728, MeOH); UV (MeOH) λmax, nm (log ε), 226 (2.58).

Halovir B
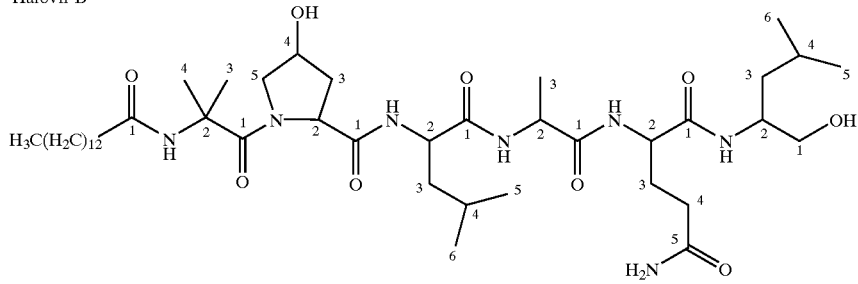
|  | C# | δ¹³C | DEPT | δ¹H (mult, J (Hz)) |
|---|---|---|---|---|
| Leucinol | 1 | 66.0 | CH₂ | 4.04(m) |
|  | 2 | 50.9 | CH | 4.61(m) |
|  | 3 | 41.3 | CH₂ | 1.76(m), 1.95(m) |
|  | 4 | 25.6 | CH | 1.85(m) |
|  | 5 | 24.3 | CH₃ | 0.99(d) |
|  | 6 | 22.7 | CH₃ | 0.99(d) |
|  | NH |  |  | 7.74(d, 8.7) |
|  | OH |  |  | 5.96 |
| Glutamine | 1 | 172.7 |  |  |
|  | 2 | 55.1 | CH | 5.05(m) |
|  | 3 | 29.4 | CH₂ | 2.95(m), 2.74(m) |
|  | 4 | 33.7 | CH₂ | 2.95(m), 2.72(m) |
|  | 5 | 175.5 |  |  |
|  | NH₂ |  |  | 8.08(s), 7.55(s) |
|  | NH |  |  | 8.01(d, 7.8) |
| Alanine | 1 | 174.1 |  |  |
|  | 2 | 51.8 | CH | 4.6(m) |
|  | 3 | 17.5 | CH₃ | 1.75(d, 5.7) |
|  | NH |  |  | 8.40(d, 6.3) |
| Leucine | 1 | 175.6 |  |  |
|  | 2 | 55.2 | CH | 4.68(m) |
|  | 3 | 40.0 | CH₂ | 2.04(m), 2.32(m) |
|  | 4 | 26.0 | CH | 2.05(m) |
|  | 5 | 24.0 | CH₃ | 1.13(d) |
|  | 6 | 21.6 | CH₃ | 1.00(d) |
|  | NH |  |  | 8.58(d, 6.3) |
| Hydroxyproline | 1 | 175.9 |  |  |
|  | 2 | 63.6 | CH | 5.26(m) |
|  | 3 | 38.4 | CH₂ | 2.73(m), 2.06(m) |
|  | 4 | 71.0 | CH | 4.77(m) |
|  | 5 | 58.2 | CH₂ | 4.33(m), 3.82(m) |
|  | OH |  |  | 7.03(bs) |
| Aib | 1 | 175.4 |  |  |
|  | 2 | 57.3 |  |  |
|  | 3 | 27.0 | CH₃ | 1.75(s) |
|  | 4 | 24.3 | CH₃ | 1.57(s) |
|  | NH |  |  | 9.64(s) |
| Tetradecanoyl chain | 1 | 174.8 |  |  |
|  | 2 | 36.2 | CH₂ | 2.54(m) |
|  | 3 | 26.3 | CH₂ | 1.80(m) |
|  | 4 | 32.6 | CH₂ | 1.24(m) |
|  | 5–12 | 30 | CH₂ | 1.2–1.4(m) |
|  | 13 | 23.4 | CH₂ | 1.2(m) |
|  | 14 | 14.8 | CH₃ | 0.87(t) |
55
HREIMS [M+Cs] m/z 970.4994; $[\alpha]_D$ -8° (c 0.247, MeOH); UV (MeOH), λmax, nm (log ε), 225 (3.01).

Halovir C

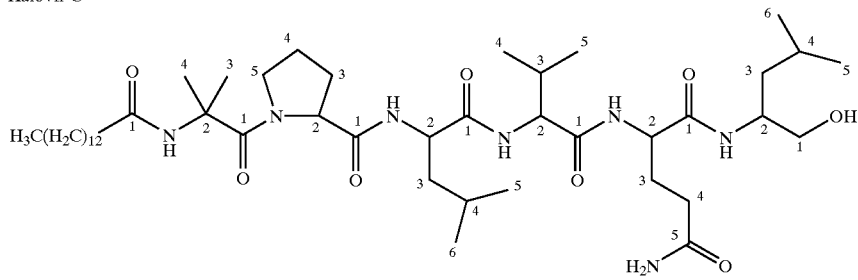

| | C# | δ¹³C | DEPT | δ¹H (mult, J (Hz)) |
|---|---|---|---|---|
| Leucinol | 1 | 65.9 | CH₂ | 4.03(m) |
| | 2 | 50.7 | CH | 4.63(m) |
| | 3 | 41.1 | CH₂ | 1.72(m), 1.95(m) |
| | 4 | 25.5 | CH | 1.97(m) |
| | 5 | 24.1 | CH₃ | 0.99(d, 6.35) |
| | 6 | 22.7 | CH₃ | 0.99(d, 6.35) |
| | NH | | | 7.78(d, 8.79) |
| | OH | | | 5.87(bs) |
| Glutamine | 1 | 172.7 | | |
| | 2 | 55.5 | CH | 5.05(m) |
| | 3 | 29.4 | CH₂ | 2.76(m), 2.94(m) |
| | 4 | 33.8 | CH₂ | 2.78(m), 2.95(m) |
| | 5 | 175.4 | | |
| | NH₂ | | | 8.14(s,), 7.62(s) |
| | NH | | | 8.13(d, 7.3) |
| Valine | 1 | 172.7 | | |
| | 2 | 61.7 | CH | 4.67(m) |
| | 3 | 30.0 | CH | 2.65(m) |
| | 4 | 19.6 | CH₃ | 1.28(d, 6.8) |
| | 5 | 20.0 | CH₃ | 1.20(d, 6.8) |
| | NH | | | 8.03(d, 7.3) |
| Leucine | 1 | 175.0 | | |
| | 2 | 55.3 | CH | 4.65(m) |
| | 3 | 40.1 | CH₂ | 2.03(m), 2.33(m) |
| | 4 | 25.9 | CH | 2.02(m) |
| | 5 | 21.5 | CH₃ | 1.12(d, 5.4) |
| | 6 | 23.9 | CH₃ | 1.00(d, 5.4) |
| | NH | | | 8.50(d, 6.35) |
| Proline | 1 | 175.0 | | |
| | 2 | 64.4 | CH | 4.77(t, 7.3) |
| | 3 | 29.7 | CH₂ | 2.31(m), 1.80(m) |
| | 4 | 26.8 | CH₂ | 1.80(m) |
| | 5 | 49.5 | CH₂ | 3.58(m), 4.0(m) |
| Aib | 1 | 174.2 | | |
| | 2 | 57.2 | | |
| | 3 | 27.2 | CH₃ | 1.78(s) |
| | 4 | 24.0 | CH₃ | 1.56(s) |
| | NH | | | 9.62(s) |
| Tetradecanoyl chain | 1 | 174.7 | | |
| | 2 | 36.2 | CH₂ | 2.51(t, 7.3) |
| | 3 | 26.2 | CH₂ | 1.77(m) |
| | 4 | 32.5 | CH₂ | 1.25(m) |
| | 5–12 | 30.0 | CH₂ | 1.2(m) |
| | 13 | 23.3 | CH₂ | 1.25(m) |
| | 14 | 14.7 | CH₃ | 0.88(t) |

HREIMS [M+Cs]⁺ m/z 982.5320; [α]$_D$ −20° (c 0.375, MeOH); UV (MeOH) λmax, nm (log ε), 227 (2.90).

Example 3

Synthesis of Halovir E

Fmoc-protected leucine attached to Wang resin with a substitution of 0.58 mmol/gram was purchased from Novabiochem, Inc. The Fmoc protecting group was removed by treating the reasin with 10 mL of 20% piperidine in anhydrous DMF for 10 minutes. The resin was suspended in solution by bubbling with argon. The solution was vacuum filtered, and the resin was washed with 3×5 mL DMF and 3×5 mL 2-propanol. A Kaiser test was performed to qualitatively ensure that a free primary amine existed. The resin was washed with 3×5 mL DMF. The first amino acid coupled to leucine was glutamine. The resin containing leucine was suspended in 10 mL of anhydrous DMF with bubbling argon and treated with 2 equivalents of N-α-Fmoc-L-glutamine (427.3 mg, 1.16 mmol), 2 equivalents of Benzotriazole-1-yl-oxy-tris-pyrrolidinophosphonium hexafluorophosphate (603.5 mg, 1.16 mmol), 1 equivalent of hydroxybenzotriazole (78.4 mg, 0.58 mmol), and 4 equivalents of N,N-Diisopropylethylamine (0.404 mL, 2.32 mmol). The coupling reaction continued until a negative result was obtained in the Kaiser test indicating the exhaustion of the free primary amine moiety. The solution was filtered, and the resin containing the newly formed dipeptide was washed with 3×5 mL of DMF.

Subsequent amino acids were added to the dipeptide by repeating the coupling reaction using the protected peptides, N-α-Fmoc-L-alanine, N-α-Fmoc-L-leucine, N-α-Fmoc-O-t-butyl-L-trans-4-hydroxyproline, and N-α-Fmoc-α-aminoisobutyric acid, in sequential order per reaction. The coupling reaction is repeated using myristic acid in place of a protected peptide. The resin was washed with 3×5 mL DMF, 3×5 ml dichloromethane, and 3×5 mL methanol; and dried overnight under vacuum.

The peptide was cleaved from the resin by treatment with 10 mL of 95% aqueous trifluoroacetic acid for one hour. The resin was filtered, and the resultant filtrate was collected. The filtrate was added dropwise to 90 mL of cold ether. A white precipitate was formed and collected, from the solution. The precipitate was washed with additional cold ether. The collected precipitate were dissolved in methanol and concentrated in vacuo to yield a white powder.

The crude peptide acid was dissolved in absolute methanol, cooled with an ice bath, and treated with diazomethane in ether until a yellow color presisted. The reaction was concentrated in vacuo to a white solid and dried under high vacuum. The desired product, Halovir E, was purified by C18 HPLC using 8% $H_2O$ in methanol.

Example 4

Synthesis of Halovir B

Following the procedure taught in Example 3, Halovir B is synthesized. Halovir E is dissolved in anhydrous THF under $N_2$ and treated with 2.0M $LiBH_4$ in THF. The reaction is refluxed for several hours, until TLC indicates a complete reaction. The reaction is quenched with 3M NaOH, and extracted in ethyl acetate. The organic phase is dried over $Na_2SO_4$, filtered and concentrated in vacuo yielding Halovir B. The compound can be further purified by HPLC, TLC, column chromatography or the like, if greater purity is desired.

Following the above procedures, Halovirs A, C and D can be synthesized in a like manner.

Example 5

Synthesis of Halovir D

To a solution of 13.3 mg of Halovir A in 0.5 mL of pyridine was added 0.5 mL of acetic anhydride and 1.2 mg of N,N-dimethylaminopyridine. The reaction mixture was stirred under nitrogen at ambient temperature for 16 hours. The solvent was removed in vacuo, and the crude mixture was partitioned between 3 mL of saturated sodium bicarbonate and 3 mL of ethyl acetate. The layers were separated and the aqueous layer was washed with 2×3 mL of ethyl acetate. The organic layers were combined and washed with 5 mL each of 1 N HCl and brine, dried over Na2CO3, filtered, and concentrated in vacuo. The crude product was purified by C18 HPLC using 2.5% H2O in methanol. Pure Halovir D was obtained as a colorless oil and was characterized by mass spectrometry, and proton and carbon NMR spectroscopy.

Example 6

Inhibition of Herpes Simplex Virus In Vitro

Antiviral activity of the halovirs was determined in vitro against the. HSV-I by an MTT assay (Hitoshi Takeuchi, An application of tetrazolium (MTT) calorimetric assay for screening of anti-herpes simplex virus compounds, Journal of Virological Methods, 33 (1991) 61–71), modified as follows. Vero cells were plated at a concentration of 10,000 cells/well in 100 μL of minimum essential medium (MEM) containing 5% fetal bovine serum (FBS) in 96-well plates. The cells were incubated overnight at 37° C. and 5% $CO_2$. The media was removed by aspiration, and 100 μL of phosphate buffered saline (PBS) was added to each well and then aspirated. The wells were treated with 100 μL of MEM containing 50 plaque forming units (pfu) of virus and incubated for one hour. Each well was then overlayed with 100 μL of media containing 2% FBS and serial dilutions of an appropriate halovir solution. The halovir solution was previously prepared by dissolving the halovir in DMSO. After incubation for five days, each well was treated with 20 μL of a solution of 10 mg/mL of MTT in PBS. The plates were incubated for four hours during which time viable cells metabolize the MTT, which resulted in insoluble blue formazan. The media was carefully aspirated, and 100 μL of acidified isopropanol was added to dissolve any formazan produced. Acidified isopropanol solution is prepared by adding 50 mL Triton X100 and 2 mL concentrated HCL to 450 mL isopropanol. The optical density of the wells at 550 nm was determined using an ELISA plate reader. The amount of formazan present is directly proportional to the number of surviving cells in a given well. The amount of formazan were spectrophotometrically measured in wells with no antiviral agent and virus to establish a quantitative standard for 100% cell survival. Similarly wells with only virus were measured and used to establish a quantitative standard for 0% cell survival. At a test concentration of 2.5 μg/mL, Halovirs A, B, C, and D protected 50%, 40%, 33%, and 55%, respectively, of the cells subjected to infection.

Example 7

Halovir A Inactivation of HSV-1 In Vitro

Halovir A in vitro inactivion of HSV-1 was demonstrated in the following example. Four experimental solutions were prepared.

Solution 1: Viral Inactivation

This experiment demonstrated in vitro inactivation of HSV-1 by Halovir A.

HSV-1 was diluted to 50,000 pfu/ml in 1.35 mL MEM with 0% Fetal Bovine Serum (0% MEM). This was treated with 8.2 μL of a solution of Halovir A dissolved in DMSO at a concentration of 25 mg/mL.

Solution 2: DMSO Inactivation Control

This experiment demonstrated that DMSO by itself does not inactivate HSV-1.

Solution 2 was prepared in an identical manner as solution 1, except that pure DMSO was added to the viral suspension.

Solution 3: Control

This experiment provides a baseline for 100% cell survival. Solution 3 was prepared with 1.35 mL 0% MEM with 8.2 μL DMSO.

Solution 4: Normal Assay Conditions

This experiment demonstrated that Halovir A is highly effective as an antiviral agent when used for direct inactivation of virus before cell infection.

Virus was diluted in 1.36 mL 0% MEM to a final concentration of 50,000 pfu/mL. No DMSO or Halovir A was added.

All solutions were vortexed for 30 seconds and then shaken at ambient temperature for 2.5 hours. They were then vortexed for 30 seconds, and 100 μL of each was diluted with 9.9 mL of 0% MEM (100×dilution). The diluted solutions are herein referred to as solutions 1–4.

96-well microtiter plates were prepared with Vero cells overnight, washed with PBS, and aspirated as previously described. 100 $\mu$L of Solution 1 was added to each well of a microtiter plate containing cells. This was repeated for Solutions 2–4. The plates were incubated at 37° C. and 5% $CO_2$. After one hour, experiment plates prepared with Solutions 1–3 were overlaid with 100 $\mu$L of 2% MEM. The experiment plate prepared with Solution 4 was overlayed with 100 $\mu$L of 2% MEM containing 1.5 $\mu$g/mL Halovir A and 0.006% DMSO. All plates were then incubated at 37° C. and 5% $CO_2$ for 5 days. The assay was worked-up with MTT as previously described.

The mean optical density at 550 nm (OD) of the wells treated with Solution 1 after work-up was 1.18. The mean was calculated using all the wells (80) applied with the solution. The mean optical densities for wells treated with Solutions 2–4 were, respectively: 0.26, 1.14, and 0.32. Therefore, there was 100% cell viabilty in wells with cells treated with solution 1. These results indicate that Halovir A inactivates HSV-1 directly before the virus is capable of infecting a Vero cell.

Although the invention has been described with reference to the examples provided above, it should be understood that various modifications can be made without departing from the spirit of the inventions. Accordingly the invention is limited only by the claims.

We claim:

1. A substantially purified compound of the structure:

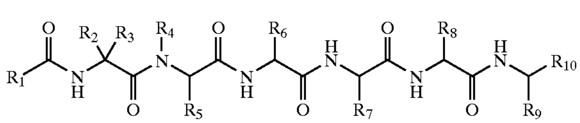

$R_1$ is tridecanyl;

$R_2$ is methyl;

$R_3$ is methyl;

$R_4$ and $R_5$ together form a 2-hydroxypropyl bridge;

$R_6$ is 2-methyl propyl;

$R_7$ is 2-propyl;

$R_8$ is 3'-propionyl acid amide;

$R_9$ is 2-methyl propyl; and $R_{10}$ is hydroxymethyl, said compound having the name designation halovir A.

2. A composition comprising a purified peptide of claim 1 in a pharmaceutically acceptable carrier.

3. The compound of claim 1, wherein:

$R_1$ is tridecanyl;

$R_2$ is methyl;

$R_3$ is methyl;

$R_4$ and $R_5$ together form a 2-hydroxypropyl bridge;

$R_6$ is 2-methyl propyl;

$R_7$ is methyl;

$R_8$ is 3'-propionyl acid amide;

$R_9$ is 2-methyl propyl; and $R_{10}$ is hydroxymethyl, said compound-having the name designation halovir B.

4. A composition comprising a purified peptide of claim 3 in a pharmaceutically acceptable carrier.

5. The composition of claim 3 wherein the composition displays inhibition of Herpes simplex virus replication in mammalian cell cultures.

6. The composition of claim 3 comprising at least one second antiviral agent selected from the group consisting of acyclovir, pencyclovir, valacyclovir, famcyclovir, gangcyclovir, nonoxynol and foscarnet.

7. The composition of claim 3, wherein the composition inactivates Herpes simplex virus.

8. The composition of claim 3, wherein topical application of the composition ameliorates infection of cells by Herpes simplex virus.

9. The compound of claim 1, wherein:

$R_1$ is tridecanyl;

$R_2$ is methyl;

$R_3$ is methyl;

$R_4$ and $R_5$ together form a propyl bridge;

$R_6$ is 2-methyl propyl;

$R_7$ is 2-propyl;

$R_8$ is 3'-propionyl acid amide;

$R_9$ is 2-methyl propyl; and $R_{10}$ is hydroxymethyl, said compound having the name designation halovir C.

10. The composition of claim 9 wherein the composition displays inhibition of Herpes simplex virus replication in mammalian cell cultures.

11. The composition of claim 9 comprising at least one second antiviral agent selected from the group consisting of acyclovir, pencyclovir, valacyclovir, famcyclovir, gangcyclovir, nonoxynol and foscarnet.

12. The composition of claim 9, wherein topical application of the composition ameliorates infection of cells by Herpes simplex virus.

13. A composition comprising a purified peptide of claim 9 in a pharmaceutically acceptable carrier.

14. The composition of claim 9, wherein the composition inactivates Herpes simplex virus.

15. The compound of claim 1, wherein:

$R_1$ is tridecanyl;

$R_2$ is methyl;

$R_3$ is methyl;

$R_4$ and $R_5$ together form a 2-acetoxypropyl bridge;

$R_6$ is 2-methyl propyl;

$R_7$ is 2-propyl;

$R_8$ is 3'-propionyl acid amide;

$R_9$ is 2-methyl propyl; and $R_{10}$ is —$CH_2$—$OC(O)CH_3$, said compound having the name designation halovir D.

16. A composition comprising a purified peptide of claim 15 in a pharmaceutically acceptable carrier.

17. The composition of claim 15, wherein the composition displays inhibition of Herpes simplex virus replication in mammalian cell cultures.

18. The composition of claim 15 comprising at least one second antiviral agent selected from the group consisting of acyclovir, pencyclovir, valacyclovir, famcyclovir, gangcyclovir, nonoxynol and foscarnet.

19. The composition of claim 15, wherein the composition inactivates Herpes simplex virus.

20. The composition of claim 15, wherein topical application of the composition ameliorates infection of cells by Herpes simplex virus.

21. The compound of claim 1, wherein:

$R_1$ is tridecanyl;

$R_2$ is methyl;

$R_3$ is methyl;

$R_4$ and $R_5$ together form a 2-hydroxypropyl bridge;

$R_6$ is 2-methyl propyl;

$R_7$ is methyl;

$R_8$ is 3'-propionyl acid amide;

$R_9$ is 2-methyl propyl; and $R_{10}$ is —$C(O)$—$OCH_3$, said compound having the name designation halovir E.

22. A composition comprising a purified peptide of claim 21 in a pharmaceutically acceptable carrier.

23. The composition of claim 21, wherein the composition displays inhibition of Herpes simplex virus replication in mammalian cell cultures.

24. The composition of claim 21 comprising at least one second antiviral agent selected from the group consisting of acyclovir, pencyclovir, valacyclovir, famcyclovir, gangcyclovir, nonoxynol and foscarnet.

25. The composition of claim 21, wherein the composition inactivates Herpes simplex virus.

26. The composition of claim 21, wherein topical application of the composition ameliorates infection of cells by Herpes simplex virus.

* * * * *